(12) United States Patent
Monteith

(10) Patent No.: US 6,218,564 B1
(45) Date of Patent: Apr. 17, 2001

(54) PROCESS FOR THE PREPARATION OF SUBSTITUTED AROMATIC COMPOUNDS

(75) Inventor: Michael John Monteith, Manchester (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/284,284

(22) PCT Filed: Sep. 19, 1997

(86) PCT No.: PCT/GB97/02553

§ 371 Date: Jun. 10, 1999

§ 102(e) Date: Jun. 10, 1999

(87) PCT Pub. No.: WO98/16486

PCT Pub. Date: Apr. 23, 1998

(30) Foreign Application Priority Data

Oct. 11, 1996 (GB) .................................................. 9621222

(51) Int. Cl.[7] .................... C07C 255/50; C07C 205/06; C07C 41/24; C07C 25/02
(52) U.S. Cl. ..................... 558/378; 568/642; 568/928; 570/201
(58) Field of Search .............. 558/378; 568/642, 568/928; 570/201

(56) References Cited

FOREIGN PATENT DOCUMENTS

| 43 40 490 | 6/1994 | (DE) . |
| 195 27 118 | 1/1997 | (DE) . |
| 94/00423 | 1/1994 | (WO) . |

OTHER PUBLICATIONS

M.B. Mitchell et al., "Coupling of heteroaryl chlorides with arylboronic acids in the presence of [1, 4–bis–(diphenylphosphine)butane]palladium(II) dichloride", Tetrahedron Letters., vol. 32, No. 20, 1991, Oxford GB, pp. 2273–2276, XP002047432.

Syun Saito et al., "A synthesis of biaryls via nickel (0)–catalysed cross–coupling reaction of chloroarenes with phenylboronic acids", Tetrahedron Letters., vol. 37, No. 17, Apr. 22, 1996, Oxford GB, pp. 2993–2996, XP002047433.

Reetz M. T. et al., "Suzuki and Heck reactions catalysed by preformed palladium clusters and palladium/nickel bimetallic clusters", Tetrahedron Letters, vol. 37, No. 26, Jun. 24, 1996, pp. 4499–4502, XP000591551.

Beller M. et al. "Palladacycles as efficient catalysts for aryl coupling reactions", Angewandte Chemie. International Edition, vol. 34, No. 17, 1995, p. 1848/1849 XP002030762.

*Primary Examiner*—Michael G. Ambrose
(74) *Attorney, Agent, or Firm*—Pillsbury Winthrop LLP

(57) ABSTRACT

A process for the preparation of a substituted aromatic compound in which a chloroaromatic compound and an alkyl-, alkenyl- or aryl-boronic acid ester or anhydride are coupled in the presence of palladium and a lipophilic aliphatic phosphine comprising at least one branched aliphatic group or a lipophilic aliphatic Dis(phosphine). Preferred phosphines include triisopropyl, triisobutyl and tricyclohexylphosphine.

18 Claims, No Drawings

PROCESS FOR THE PREPARATION OF SUBSTITUTED AROMATIC COMPOUNDS

This application is the national phase of international application PCT/GB97/02553 filed Sep. 19, 1997 which designated the U.S.

This invention relates to a process for preparing substituted aromatic compounds.

Many of the currently available processes for making substituted aromatic compounds necessarily rely upon coupling reactions involving bromo- and iodo-substituted intermediates. These intermediates can be difficult to prepare and expensive.

For example the paper by Suzuki et al in Synthetic Communications, 11(7), 513–519 (1981) describes the coupling of certain aryl boronic acids with iodo- or bromo-benzenes in the presence of $Pd(0)(PPh_3)_4$ and $Na_2CO_3$. At the foot of page 515 and on page 516, lines 16–17, the paper teaches that the coupling does not work with chloroarenes and chlorobenzenes.

European Patent No. 0 470 795 B1 describes a process for the manufacture of biphenylcarbonitriles wherein certain phenylboronic acids are coupled with cyanophenyl compounds having a bromo, iodo or trifluoromethanesulphonyloxy group in the presence of specified catalysts.

We have now invented a process which uses chloroaromatic compounds and avoids the need for $Pd(0)(PPh_3)_4$, which is itself rather expensive. Chloroaromatic compounds are generally easier to prepare and cheaper than the corresponding bromo-, iodo- and trifluoromethanesulphonyloxy compounds.

According to the present invention there is provided a process for the preparation of a substituted aromatic compound comprising coupling a chloroaromatic compound and an alkyl-, alkenyl- or aryl-boronic acid, ester or anhydride in the presence of palladium and a phosphine selected from the group consisting of:
  a) lipophilic aliphatic phosphines comprising at least one branched aliphatic group, and
  b) lipophilic aliphatic bis(phosphines).

The chloroaromatic compound is preferably an optionally substituted chlorobenzene, chloropyridine, chiorotriazole, chlorobenzotriazole, chloronaphthalene, chlorothiophene, chloropyrimidine, chlorofuran or chlorobenzofuran, more preferably an optionally substituted chlorobenzene, especially an optionally substituted chlorobenzene which is free from iodo, bromo and trifluoromethanesulphonyloxy groups. Especially preferred substituted chlorobenzenes have one, two or three substituents selected from alkyl, preferably $C_{1-4}$-alkyl; alkoxy, preferably $C_{1-4}$-alkoxy; nitro; fluoro, chloro; cyano; carboxy; $-OCF_3$; $-NR^1R^2$ wherein $R^1$ and $R^2$ are each independently H, $C_{1-4}$-alkyl or $-CO-(C_{1-4}$-alkyl); $-SR^1$; $-SO_3H$; OH; $OCOR^3$ wherein $R^3$ is $C_{1-4}$-alkyl or aryl; $COR^1$, particularly formyl, and $CF_3$.

Examples of chloroaromatic compounds include chlorobenzene, 2-chloronaphthalene, 2-cyano chlorobenzene, 4-formyl chlorobenzene, 2-chloropyridine, 2-chloropyrimidine, 2-chlorothiophene, methyl 2-chlorobenzoate, 4-chloroaniline, 1,4-dichlorobenzene, 1-chloro-3-nitrobenzene, 4-chloro-2-nitrophenol, 4-chloro-3-nitrobenzene sulphonic acid, 5-chlorobenzotriazole and 1-chloro-2,4-dinitrobenzene. Many more chioroaromatic compounds are known and may be used in the process. The most preferred chloroaromatic compound is 2-cyano chlorobenzene.

The alkyl-, alkenyl- or aryl-boronic acid, ester or anhydride is preferably of the Formula (1):

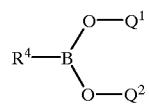

(1)

wherein:
  $R^4$ is alkyl, alkenyl or aryl; and
  $Q^1$ and $Q^2$ are each independently H, alkyl, alkenyl or aryl or $Q^1$ and $Q^2$ together with the $-O-B-O-$ group which joins them forms a boroxin ring of the Formula (2) wherein $R^4$ is as hereinbefore defined:

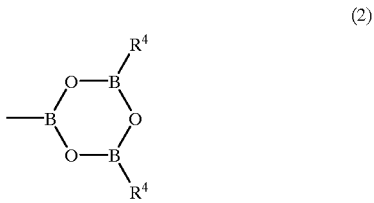

(2)

When $R^4$, $Q^1$ or $Q^2$ is alkyl it is preferably $C_{1-10}$-alkyl more preferably $C_{1-4}$-alkyl.

When $R^4$, $Q^1$ or $Q^2$ is alkenyl it is preferably $C_{2-10}$-alkenyl, more preferably $C_{2-4}$-alkenyl, especially $-CH=CH_2$ or $-C(CH_3)=CH_2$.

When $R^4$, $Q^1$ or $Q^2$ is aryl it is preferably optionally substituted phenyl, more preferably phenyl or phenyl bearing one, two or three substituents selected from those mentioned above for the chloroaromatic compound.

When $R^4$, $Q^1$ or $Q^2$ is heteroaryl it is preferably pyridinyl, naphthalenyl, thiophenyl, pyrimidinyl or furanyl, optionally substituted by one or two substituents selected from those mentioned above for the chloroaromatic compound.

Preferably $Q^1$ and $Q^2$ are both H or $Q^1$ and $Q^2$ together with the $-O-B-O-$ group which joins them forms a boroxin ring of the Formula (2) shown above. $R^4$ is preferably optionally substituted phenyl wherein the optional substituents are as described above.

Examples of preferred alkyl-, alkenyl- and aryl boronic acids include benzeneboronic acid, n-butaneboronic acid, thiophene-2-boronic acid, thiophene-3-boronic acid, 4-methylbenzeneboronic acid, 3-methylthiophene-2-boronic acid, 3-aminobenzeneboronic acid monohydrate, 3-aminobenzeneboronic acid hemisulphate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 4-bromobenzeneboronic acid, 3,5-bis(trifluoromethyl) benzeneboronic acid, 1,4-benzenediboronic acid, 4,4'-biphenyldiboronic acid, and the esters and anhydrides of such acids.

The boronic acids readily undergo dehydration to form cyclic trimeric anhydrides known as boroxines. This often occurs spontaneously at room temperature, but it does not affect the reaction because both the acid and anhydride and mixtures of the two will work in the process.

Compounds of Formula (1) are known and may be prepared as needed or purchased from commercial sources, for example Lancaster Synthesis, United Kingdom. Known synthetic methods include reaction of a trialkylboronate of the formula $B(OR)_3$ wherein R is a $C_{1-6}$-alkyl group with a Grignard reagent or phenyl lithium compound of the $R^4$ group described above (e.g. $R^4Li$ or $R^4MgX$ wherein X is a halogen). Such procedures are described in our EP 0 470 795 B1, page 3, lines 23–38, which is incorporated herein by reference thereto. Aryl boronic acids of Formula (1) having a wide variety of substituents may also be prepared by functionalisation of the parent aryl boronic acid or ester, e.g. by nitration, oxidation and halogenation. Functionalisation methods are described by T. Onak in "Organoborane Chemistry", Academic Press, New York, 1975, Page 222.

Lipophilic aliphatic phosphines can be obtained from commercial sources (e.g. Sigma, Aldrich, Fluka and other chemical catalogue companies) or they can be prepared using generally known processes. These phosphines are believed to act as ligands to the palladium thereby forming an effective catalyst for the coupling reaction.

The lipophilic aliphatic phosphines comprising at least one branched liphatic group or aliphatic bis(phopshines) preferably comprise from five to forty, preferably from five to thirty, especially from six to twenty five aliphatic carbon atoms. Most preferably, each of the phosphorus atoms is substituted by three aliphatic groups. The point of branching in the aliphatic groups is most commonly at the carbon alpha or beta to the phosphorus atom. Preferred lipophilic aliphatic phosphines are of the Formula (3) or (4):

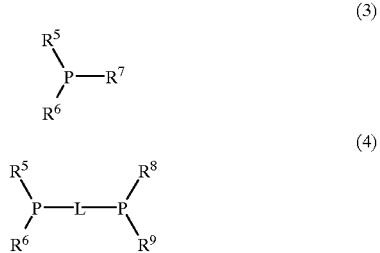

wherein:
each $R^5$, $R^6$, $R^7$, $R^8$ and $R^9$ independently is an alkyl or cycloalkyl group, provided that in the phosphines of formula (3), at least one of $R^{5-7}$ is branched; and
L is a divalent aliphatic linker group.

When $R^5$, $R^6$, $R^7$, $R^8$ or $R^9$ is an alkyl group it is preferably straight chain or branched chain $C_{1-6}$-alkyl, more preferably branched chain $C_{3-6}$-alkyl.

When $R^5$, $R^6$, $R^7$, $R^8$ or $R^9$ is a cycloalkyl group it is preferably cyclohexyl or cyclopentyl.

L is preferably a $C_{1-20}$-alkylene group, more preferably a $C_{1-10}$-alkylene group, especially a $C_{2-6}$-alkylene group, more especially —$(CH_2)_2$—, —$(CH_2)_3$—, —$(CH_2)_4$— or —$(CH_2)_5$—.

In the phosphines of Formula (3), often two, and most often three of the groups represented by $R^5$, $R^6$ and $R^7$ are branched. It is preferred that the groups represented by $R^5$, $R^6$ and $R^7$ are identical and, preferably, they are branched chain $C_{3-6}$-alkyl or cyclohexyl, especially isopropyl, isobutyl or cyclohexyl.

Examples of lipophilic aliphatic phosphine ligands of Formula (3) include: triisopropylphosphine, triisobutylphosphine, tri-tert-butylphosphine, tripentyl phosphines, such as tri-iso-, tri-tert- and tricyclopentyl phosphine, and trihexyl phosphines, such as tri- iso-, tri-tert- and tricyclohexylphosphine, especially triisopropyl phosphine, triisobutyl phosphine and tricyclohexyl phosphine.

In the preferred phosphines of Formula (4) the groups represented by $R^5$, $R^6$, $R^8$ and $R^9$ are identical, especially $C_{3-6}$-alkyl or cyclohexyl, and L is $C_{2-6}$-alkylene.

Examples of lipophilic aliphatic phosphine ligands of Formula (4) include:
1,2-bis(dimethylphosphine)ethane, 1,2-bis (diethylphosphine)ethane,
1,2-bis(dipropylphosphine)ethane, 1,2-bis (diisopropylphosphine)ethane,
1,2-bis(dibutylphosphine)ethane, 1,2-bis (dicyclohexylphosphine)ethane,
1,3-bis(dicyclohexylphosphine)propane, 1,3-bis (diisoproppylphospine)propane,
1,4-bis(diisopropylphosphine)butane and 2,4-bis (dicyclohexylphospine)pentane.

The mole ratio of alkyl-, alkenyl- or aryl-boronic acid, ester or anhydride to chloroaromatic compound will vary depending on the number of aromatic chloro groups in the chloroaromatic compound and the number of couplings it is desired to achieve. For a single coupling, the mole ratio is usually from 1:1 to 1.5:1, whereas for a double coupling, the mole ratio is usually from 2:1 to 2.5:1. In many embodiments, only a single coupling is desired, and the mole ratio of alkyl-, alkenyl- or aryl-boronic acid, ester or anhydride to chloroaromatic compound is from 1:1 to 1.3:1, and in certain preferred embodiments, especially when a phosphate is employed as a base, the mole ratio is preferably 1:1.

The palladium may be derived from a convenient palladium source, for example, palladium halides, especially $PdCl_2$, $PdBr_2$ and $PdI_2$, palladium carboxylates, especially $Pd(CH_3CO_2)_2$, $Pd(CF_3CO_2)_2$ and palladium (II) acetylacetonoate, $Pd(NO_3)_2$, PdO, $PdSO_4$, and palladium (II) bis(benzonitrile)dichloride or, if desired, from palladium on carbon. Still further sources of palladium will be apparent to those of ordinary still in the art. It is believed that where Pd(II) ions are derived from these sources, the Pd(II) is converted to Pd(0) in situ during the course of the process.

The quantity of palladium used in the process is preferably in the range 0.0001 to 10 mole %, more preferably 0.005 to 5 mole %, especially 0.01 to 3 mole %, relative to the quantity of chloroaromatic compound.

The quantity of lipophilic aliphatic phosphine used in the process is preferably such that the molar ratio of palladium: phosphorus is from 1:0.8 to 1:10, more preferably 1:09 to 1:5, especially about 1:2.4. As will be apparent, phosphines of Formula (4) contain two phosphorus atoms per molecule whereas those of Formula (3) contain one phosphorus atom per molecule.

The process of the invention is preferably performed in the presence of a base. Suitable inorganic bases include, for example, alkali metal and alkaline earth metal salts of weak acids, preferably alkali metal and alkaline earth metal hydrogencarbonates, carbonates and/or phosphates, which may be hydrated or anhydrous, but are preferably hydrated, especially when a phosphate is employed as a base. Specific examples of suitable inorganic bases include CsF, $K_2CO_3$, $KHCO_3$, $NaHCO_3$, KOH, NaOH, $Na_3PO_4$ and $K_3PO_4$. Sodium carbonate, $Na_3PO_4$ and $K_3PO_4$ are particularly preferred. Suitable organic bases include amines, particularly triethylamine and tributylamine, and carboxylates, such as sodium and potassium acetate or propionate.

The ratio of chloroaromatic compound to inorganic base is preferably chosen such that from 0.3 to 2, more preferably from 0.4 to 1.3, equivalents of inorganic base are employed per mole of chloroaromatic compound. If, however, the chloroaromatic compound contains a further halogen atom the preferred amount of inorganic base is double that previously stated.

The process is preferably performed in a solvent. Preferred solvents are organic solvents, especially hydrocarbons (e.g. toluene or xylene), ethers (e.g. tetrahydrofuran and diglyme), alcohols, such as $C_{4-8}$ aliphatic alcohols, especially pentanol and hexanol and isomers thereof, cyclohexanol, polar aprotic solvents (e.g. N-methyl pyrrolidone, dimethylformamide, N,N-dimethylacetamide or dimethyl sulphoxide) and mixtures thereof. Solvents having a boiling point above 99° C., especially in the range 100–200° C., are preferred. N,N-dimethylacetamide and N-methyl pyrrolidone are particularly preferred solvents.

The process is preferably performed at a temperature in the range 50° C. to 200° C., more preferably 80° C. to 180° C., especially 100° C. to 160° C., and most especially from 140° to 155° C. Normally atmospheric pressure is used although elevated pressure may be used if desired, for example when the component of the mixture boils below the temperature at which the process is performed.

A preferred embodiment of the present invention provides a process for the preparation of a substituted aromatic compound comprising coupling a chloroaromatic compound and an alkyl-, alkenyl- or aryl-boronic acid, ester or anhydride of the Formula (1) as hereinbefore defined, in the presence of palladium and a lipophilic aliphatic phosphine of Formula (3) or (4) as hereinbefore defined. It is further preferred that the quantity of palladium is in the range 0.005 to 5 mole %, and especially from 0.1 to 2 mole %, relative to the quantity of chloroaromatic compound, the quantity of said lipophilic aliphatic phosphine used is such that the molar ratio of palladium: phosphorus is from 1:0.8 to 1:10, the process is performed in a solvent and that the temperature is, preferably, in the range 140° C. to 200° C.

During the course of the process the alkyl-, alkenyl- or aryl- group of the boronic acid, ester or anhydride replaces the chloro- atom of the chloroaromatic compound. Thus the identity of the substituent on the resultant substituted aromatic compound is the same as the alkyl-, alkenyl or aryl-group in the starting boronic acid, ester or anhydride. For example an alkyl boronic acid leads to an aromatic compound having an alkyl substituent, an alkenyl boronic acid leads to an aromatic compound having an alkenyl substituent and an aryl boronic acid leads to an aromatic compound having an aryl substituent. Preferably the substituted aromatic compound is a substituted biphenyl.

As will be understood, the term "alkyl-, alkenyl- or aryl-boronic acid, ester or anhydride" is used in this specification as an abbreviation for alkyl boronic acid, alkenyl boronic acid, aryl boronic acid and esters and anhydrides of alkyl boronic acid, alkenyl boronic acid and aryl boronic acid. References to boronic acids include the free acid and salt forms.

It is surprising that the present process works at all in view of the above mentioned Suzuki et al paper teaching that the halo aromatic used in Pd(0)(PPh$_3$)$_4$ catalysed couplings must contain a bromo or iodo atom. Furthermore, as chloroaromatics are cheap, readily accessible and environmentally friendly, the present process has great economic advantages over the Suzuki et al reaction.

The present process may be used to prepare a wide range of intermediates of value in the fine chemical, pharmaceutical and agrochemical industries, for example angiotensin II inhibitors described in our EP 253310 and terphenyls used in liquid crystal displays (PCT/GB88/00880).

The invention is further illustrated by the following examples in which all parts and percentages are by weight unless specified otherwise.

EXAMPLE 1

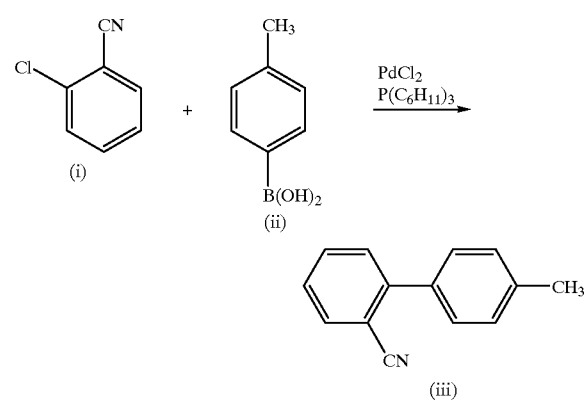

A mixture of (i) (1.38 g, 0.01 moles), (ii) (from Lancaster Synthesis, 1.70 g, 0.0126 moles), sodium carbonate (1.33 g, 0.0126 moles), PdCl$_2$ (0.0186 g, 1.05×10$^{-4}$ moles), P(C$_6$H$_{11}$)$_3$ (a lipophilic aliphatic phosphine having 15 —CH$_2$— groups, 0.0701 g, 2.5×10$^{-4}$ moles) and N-methylpyrrolidone (10 cm$^3$) were heated to 140–150° C. under nitrogen for 4 hours. The product (iii) was obtained in a conversion of 81%, as measured by gas chromatography relative to the amount of starting material.

EXAMPLE 2

Example 1 was repeated except that in place of PdCl$_2$ there was used Pd(OCOCH$_3$)$_2$ (0.02369, 1.05×10$^{-4}$ moles). The product (iii) was obtained in a conversion of 94%, as measured by gas chromatography relative to the amount of starting material.

EXAMPLE 3

Example 1 was repeated except that in place of N-methylpyrrolidone there was used diglyme. Product (iii) was obtained in a conversion of 49%, as measured by gas chromatography relative to the amount of starting material.

EXAMPLE 4

Example 1 was repeated except that in place of N-methylpyrrolidone there was used N,N-dimethylacetamide. The product (iii) was obtained in a conversion of 97%, as measured by gas chromatography relative to the amount of starting material.

EXAMPLE 5

A mixture of 2-chlorobenzonitrile (1.38 g, 0.01 moles), 4-methylbenzene boronic acid (1.70 g, 0.0126 moles), sodium carbonate (0.53 g, 0.0126 moles), Pd(OAc)$_2$ (0.004 g, 1.78×10$^{-5}$ moles), P(C$_6$H$_{11}$)$_3$ (0.012 g, 4.28×10$^{-5}$ moles) was added to N-methylpyrrolidone (10 cm$^3$) and heated to 140–150° C. under nitrogen for 5 hours. The conversion to 4'-methyl-2-cyanobiphenyl, as measured by gas chromatography relative to the amount of starting material, was 65%.

EXAMPLE 6

The method of Example 5 was followed, except that $PdCl_2$ (0.0313 g, $1.76 \times 10^{-4}$ moles) was used in place of the $Pd(OAc)_2$, the amount of tricyclohexyl phosphine employed was 0.1239 g ($4.4 \times 10^{-4}$ moles), and the reaction was carried out at 140–150° C. under nitrogen for 4 hours. The conversion to 4'-methyl-2-cyanobiphenyl, as measured by gas chromatography relative to the amount of starting material, was 91.3%.

EXAMPLE 7

The method of Example 6 was followed, except that 0.0177 g, ($1 \times 10^{-4}$ moles) of $PdCl_2$ was used, the amount of tricyclohexyl phosphine employed was 0.068 g ($2.42 \times 10^{-4}$ moles), the amount of sodium carbonate used was 1.33 g (0.0125 moles), and the reaction was carried out at 140–150° C. under nitrogen for 2 hours. The conversion to 4'-methyl-2-cyanobiphenyl, as measured by gas chromatography relative to the amount of starting material, was 91%.

EXAMPLE 8

The method of Example 7 was followed, except that 0.0187 g, ($1.05 \times 10^{-4}$ moles) of $PdCl_2$ was used, the amount of tricyclohexyl phosphine employed was 0.07 g ($2.5 \times 10^{-4}$ moles), dimethyl acetamide (10 ml) was employed in place of the N-methylpyrrolidone, and the reaction was carried out at 140–150° C. under nitrogen for 6 hours. The conversion to 4'-methyl-2-cyanobiphenyl, as measured by gas chromatography relative to the amount of starting material, was 98%.

EXAMPLE 9

A mixture of 2-chlorobenzonitrile (0.688 g, 0.005 moles), 4-methylbenzene boronic acid (0.856 g, 0.0063 moles), sodium carbonate (0.668 g, 0.0063 moles), $PdCl_2$ (0.00886 g, $5 \times 10^{-5}$ moles), triisobutylphosphine (0.0565 g of 43% w/w solution in toluene, $1.2 \times 10^{-5}$ moles) was added to N-methylpyrrolidone (5 cm$^3$) and heated to 150° C. under nitrogen for 6 hours. The conversion to 4'-methyl-2-cyanobiphenyl, as measured by gas chromatography relative to the amount of starting material, was 89%.

EXAMPLE 10

The method of Example 9 was followed, except that $K_3PO_4 \cdot H_2O$ (1.451 g, 0.0063 moles) was employed in place of the sodium carbonate, and the reaction was carried out at 150° C. under nitrogen for 4 hours. The conversion to 4'-methyl-2-cyanobiphenyl, as measured by gas chromatography relative to the amount of starting material, was 98%.

EXAMPLE 11

The method of Example 10 was followed, except that $Na_3PO_4 \cdot 12H_2O$ (1.597 g, 0.0042 moles) was employed in place of the potassium phosphate. The conversion to 4'-methyl-2-cyanobiphenyl, as measured by gas chromatography relative to the amount of starting material, was 96%.

EXAMPLE 12

The method of Example 10 was followed, except that the amount of 4-methylbenzene boronic acid used was (0.68 g, 0.0005 moles), and the reaction was carried out at 150° C. under nitrogen for 6 hours. The conversion to 4'-methyl-2-cyanobiphenyl, as measured by gas chromatography relative to the amount of starting material, was ca. 100%.

EXAMPLE 13

The method of Example 11 was followed, except that the amount of 4-methylbenzene boronic acid used was (0.68 g, 0.0005 moles), and the reaction was carried out at 150° C. under nitrogen for 4.5 hours. The conversion to 4'-methyl-2-cyanobiphenyl, as measured by gas chromatography relative to the amount of starting material, was 95%.

EXAMPLE 14

A mixture of 1,4-dichlorobenzene (0.735 g, 0.005 mole), 4-methylbenzene boronic acid (0.851 g, 0.0063 mole), sodium carbonate (0.6684 g, 0.0063 mole), $PdCl_2$ (0.0089 g, $5 \times 10^{-5}$ mole) and tricyclohexylphosphine (0.0339 g, $1.2 \times 10^{-4}$ mole) in N-methyl pyrrolidone (5 ml) under $N_2$ was heated to 150° C. for 5 h. The conversion to 4'-methyl-2-chlorobiphenyl, as measured by gas chromatography relative to the amount of starting material, was 76%.

EXAMPLE 15

A mixture of 2-chlorobenzonitrile (0.7 g, 0.005 mole), 4-methoxybenzeneboronic acid (0.962 g, 0.0063 mole), sodium carbonate (0.6684 g, 0.0063 mole), $PdCl_2$ (0.009 g, $5 \times 10^{-5}$ mole) and tricyclohexyl phosphine (0.0348 g, $1.24 \times 10^{-4}$ mole) under $N_2$ in N-methyl pyrrolidone (5 ml) was heated at 150° C. for 4 hours and the conversion to 4'-methoxy-2-chlorobiphenyl, as measured by gas chromatography relative to the amount of starting material, was 77%.

EXAMPLE 16

A mixture of 4-chloronitrobenzene (0.789 g, 0.005 mole), 4-methylbenzene boronic acid (0.857 g, 0.0063 mole), sodium carbonate (0.6708 g, 0.0063 mol), $PdCl_2$ (0.0088 g, $5 \times 10^{-5}$ mole) and tricyclohexyl phosphine (0.0337 g, $1.2 \times 10^{-4}$ mole) in N-methyl pyrrolidone (5 ml) under $N_2$ was heated at 150° C. for 3.5 hours and the conversion to 4'-methyl-2-nitrobiphenyl, as measured by gas chromatography relative to the amount of starting material, was 100%.

Comparison A

Example 1 was repeated except that in place of $P(C_6H_{11})_3$ there was used $P(OC_2H_5)_3$ (0.0415 g, $2.5 \times 10^{-4}$ moles). The product (iii) was obtained in a conversion of only 27.4%, as measured by gas chromatography relative to the amount of starting material.

Comparison B

Example 1 was repeated except that in place of $P(C_6H_{11})_3$ there was used $P(nC_4H_9)_3$ (0.0505 g, $2.5 \times 10^{-4}$ moles). The product (iii) was obtained in a conversion of only 16%, as measured by gas chromatography relative to the amount of starting material.

Comparison C

Example 1 was repeated except that in place of $P(C_6H_{11})_3$ there was used $PPh_3$ (0.0655 g, $2.5 \times 10^{-4}$ moles). The product (iii) was obtained in a conversion of only 41%, as measured by gas chromatography relative to the amount of starting material.

Comparison D

Example 14 was repeated, except that the triisobutyl phosphine was omitted. After 4 hours at 150° C., the conversion to 4'-methyl-2-cyanobiphenyl, as measured by gas chromatography relative to the amount of starting material, was only 63%.

What is claimed is:

1. A process for the preparation of a substituted aromatic compound comprising coupling a chloroaromatic compound and an alkyl-, alkenyl- or aryl-boronic acid, ester or anhydride in the presence of palladium and a phosphine selected from the group consisting of:

a) lipophilic aliphatic phosphines comprising at least one branched aliphatic group, and
   b) lipophilic aliphatic bis(phosphines); wherein the process is performed in the presence of a base selected from an alkali metal phosphate and an alkaline earth metal phosphate.

2. A process according to claim 1 wherein the base is sodium phosphate or potassium phosphate.

3. A process according to either claim 1 or claim 2 wherein the base is hydrated.

4. A process according to either claim 1 or claim 2 wherein the lipophilic aliphatic phosphine has from five to forty aliphatic carbon atoms.

5. A process according to either claim 1 or claim 2 wherein the lipophilic aliphatic phosphine is of the formula (3) or (4):

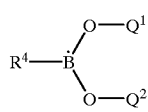

wherein:

each $R^5$, $R^6$, $R^7$, $R^8$ and $R^9$ is an alkyl or cycloalkyl group; and

L is a divalent aliphatic linker group.

6. A process according to either claim 1 or claim 2 wherein the lipophilic aliphatic phosphine is triisopropyl phosphine, triisobutylphosphine or tricyclohexylphosphine.

7. A process according to claim 1 or 2 wherein the alkyl-, alkenyl- or aryl-boronic acid, ester or anhydride is of the Formula (1):

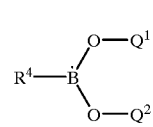

wherein:

$R^4$ is alkyl, alkenyl or aryl; and $Q^1$ and $Q^2$ are each independently H, alkyl, alkenyl or aryl or $Q^1$ and $Q^2$ together with the —O—B—O— group which joins them forms a boroxin ring of the Formula (2) wherein $R^4$ is as hereinbefore defined:

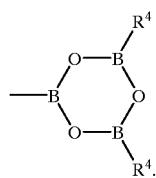

8. A process according to claim 1 or 2 wherein the alkyl-, alkenyl- or aryl-boronic acid, ester or anhydride is of the Formula (1):

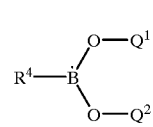

wherein:

$R^4$ is alkyl, alkenyl or aryl; and $Q^1$ and $Q^2$ are both H or $Q^1$ and $Q^2$ together with the —O—B—O— group which joins them forms a boroxin ring of the Formula (2) wherein $R^4$ is as hereinbefore defined:

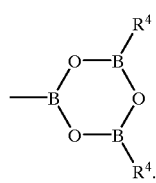

9. A process according to claim 1 or 2 wherein the quantity of palladium used in the process is in the range 0.0001 to 10 mole % relative to the quantity of chloroaromatic compound.

10. A process according to claim 1 or 2 wherein the quantity of lipophilic aliphatic phosphine used in the process is such that the molar ratio of palladium:phosphorus is from 1:0.8 to 1:10.

11. A process according to claim 1 or 2 which is performed in a solvent.

12. A process according to any one of claim 1 or 2 which is performed in a solvent comprising N,N-dimethyl acetamide.

13. A process according to claim 1 or 2 which is performed at a temperature in the range 50° C. to 200° C.

14. A process according to claim 1 wherein:

(i) the alkyl-, alkenyl-, or aryl-boronic acid, ester or anhydride is of Formula (1)

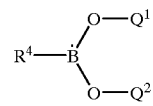

wherein $R^4$ is alkyl, alkenyl or aryl; and $Q^1$ and $Q^2$ are each independently H, alkyl, alkenyl or aryl or $Q^1$ and $Q^2$ together with the —O—B—O— group which joins them forms a boroxin ring of the Formula (2) wherein $R^4$ is as hereinbefore defined:

(2)

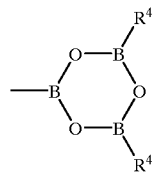

(ii) the lipophilic aliphatic phosphine is of Formula (3) or (4)

(3)

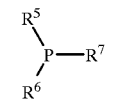

(4)

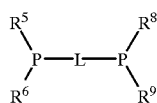

wherein each $R^5$, $R^6$, $R^7$, $R^8$ and $R^9$ is an alkyl or cycloalkyl group; and L is a divalent aliphatic linker group;

(iii) the quantity of palladium is in the range 0.005 to 5 mole % relative to the quantity of chloroaromatic compound;

(iv) the quantity of said lipophilic aliphatic phosphine is such that the molar ratio of palladium:phosphorus is from 1:08 to 1:10;

(v) the process is performed in a solvent; and (vi) the process is performed at a temperature in the range of from 140° C. to 200° C.

15. A process according to claim 8 for the preparation of 4-methyl-2'-cyanobiphenyl comprising coupling 2-cyano chlorobenzene and a boronic acid, ester or anhydride of Formula (1):

(1)

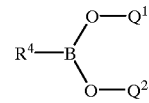

wherein:

$Q^1$ and $Q^2$ are each independently H; or $Q^1$ and $Q^2$ together with the —O—B—O— group which joins them forms a boroxin ring of the Formula (2):

(2)

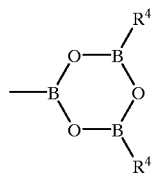

wherein $R^4$ is 4-methylphenyl.

16. A process according to claim 15 wherein the liophilic aliphatic phosphine is triisopropyl phosphine, triisobutyl phosphine or tricyclohexyl phosphine.

17. A process according to one of claims 1, 2, or 15 or in which the mole ratio of alkyl-, alkenyl- or aryl-boronic acid, ester or anhydride to chloroaromatic compound is from 1:1 to 1.3:1.

18. A process according to claim 15 or 16 which is performed in the presence of a base selected from the group consisting of sodium carbonate, sodium phosphate or potassium phosphate.

* * * * *